US011311402B2

(12) United States Patent
Perez et al.

(10) Patent No.: US 11,311,402 B2
(45) Date of Patent: *Apr. 26, 2022

(54) SCOLIOSIS BRACE

(71) Applicant: Fiji Manufacturing, LLC, Irvine, CA (US)

(72) Inventors: Joel Perez, Long Beach, CA (US); Geoffrey Garth, Long Beach, CA (US); Steven Burke, Huntington Beach, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/888,117

(22) Filed: May 6, 2013

(65) Prior Publication Data

US 2014/0330187 A1 Nov. 6, 2014

(51) Int. Cl.
*A61F 5/02* (2006.01)
*A61F 5/03* (2006.01)

(52) U.S. Cl.
CPC ............. *A61F 5/024* (2013.01); *A61F 5/028* (2013.01)

(58) Field of Classification Search
CPC .... A61F 5/00; A61F 5/01; A61F 5/022; A61F 5/024; A61F 5/026; A61F 5/028; A61F 5/26; A61F 5/30; A61F 5/32; A61F 5/0193; A61F 5/058–05833; A61F 13/14–148; A61F 5/02–05833; A61F 5/24–37
USPC ..... 128/95.1, 96.1, 98.1, 99.1, 100.1, 102.1, 128/112.1, 846, 869, 870, 873, 876; 602/5, 12, 19, 60, 75
See application file for complete search history.

(56) References Cited

U.S. PATENT DOCUMENTS

| 492,903 | A | * | 3/1893 | Gerlitz | A61F 5/028 2/44 |
| 1,257,297 | A | * | 2/1918 | Brown | A61F 5/0123 602/16 |
| 1,562,935 | A | * | 11/1925 | Whisner | A61F 5/02 602/19 |
| 1,931,990 | A | | 10/1933 | Massek | |
| 1,935,859 | A | * | 11/1933 | Putz | A61F 5/024 602/19 |

(Continued)

FOREIGN PATENT DOCUMENTS

| CA | 2175469 C | 6/1995 |
| DE | 19850993 A1 | 4/1999 |

(Continued)

OTHER PUBLICATIONS http://www.scoliosisjournal.com—Figure; Figure 2, Example of a double major scoliosis treated with a Cheneau light brace, printed on Dec. 12, 2012 at 4:26 pm.

*Primary Examiner* — Michelle J Lee
(74) *Attorney, Agent, or Firm* — Fish IP Law, LLP (57) ABSTRACT

A brace comprises a belt and removably attachable vertical strut(s). Each vertical strut can comprise one or more of a strut(s), thoracic pad(s), hip pad(s), lumbar support pad(s), chest support pad(s), de-rotation pad(s), or any other component suitable to assist or restrict movement of a wearer's body, reduce or apply a force to a wearer's body, correct the shape of a wearer's body, reduce pain, or provide support to a wearer's body. It is contemplated that each component can be removable or adjustable from a vertical strut or belt.

8 Claims, 10 Drawing Sheets

(56) References Cited

U.S. PATENT DOCUMENTS

| | | | | |
|---|---|---|---|---|
| 2,187,323 A * | 1/1940 | Kelton | A61F 5/05808 | 602/20 |
| 2,191,283 A * | 2/1940 | Longfellow | A61F 5/3753 | 602/16 |
| 2,687,129 A * | 8/1954 | Talkish | A61F 5/024 | 602/19 |
| 2,760,486 A | 8/1956 | Ward | | |
| 2,808,050 A * | 10/1957 | Ward | | 602/19 |
| 3,094,984 A * | 6/1963 | Jewett | A61F 5/024 | 602/19 |
| 3,351,053 A * | 11/1967 | Stuttle | A61F 5/024 | 602/19 |
| 3,548,817 A * | 12/1970 | Mittasch | A61F 5/024 | 602/36 |
| 3,945,376 A * | 3/1976 | Kuehnegger | A61F 5/026 | 602/19 |
| 4,202,327 A * | 5/1980 | Glancy | A61F 5/022 | 602/19 |
| 4,230,101 A | 10/1980 | Gold | | |
| 4,285,336 A | 8/1981 | Oebser | | |
| 4,640,269 A * | 2/1987 | Goins | | 602/19 |
| 4,691,696 A * | 9/1987 | Farfan de los Godos | A61F 5/028 | 128/95.1 |
| 4,907,575 A * | 3/1990 | Satterthwaite | A61F 5/024 | 602/19 |
| 4,976,257 A * | 12/1990 | Akin | A61F 5/024 | 602/19 |
| 5,012,798 A | 5/1991 | Graf | | |
| 5,135,471 A * | 8/1992 | Houswerth | A61F 5/024 | 128/102.1 |
| 5,244,924 A * | 9/1993 | Meinert | A61K 31/02 | 514/672 |
| 5,405,313 A * | 4/1995 | Albin | A61F 5/026 | 602/19 |
| 5,449,338 A * | 9/1995 | Trudell | A61F 5/024 | 602/19 |
| 5,462,518 A | 10/1995 | Hatley | | |
| 5,503,621 A * | 4/1996 | Miller | A61F 5/022 | 2/44 |
| 5,538,499 A * | 7/1996 | Schwenn | A61F 5/3753 | 602/16 |
| 5,599,286 A | 2/1997 | Labelle | | |
| 5,632,724 A * | 5/1997 | Lerman | A61F 5/024 | 128/845 |
| 6,039,707 A * | 3/2000 | Crawford | A61F 5/0193 | 602/18 |
| 6,190,343 B1 * | 2/2001 | Heinz et al. | | 602/19 |
| 6,436,065 B1 * | 8/2002 | Mitchell | A61F 5/01 | 2/44 |
| 6,471,665 B1 | 10/2002 | Milbourn | | |
| 6,605,052 B1 * | 8/2003 | Cool | A61F 5/024 | 128/102.1 |
| 6,790,191 B1 * | 9/2004 | Hendricks | | 602/19 |
| 6,893,411 B1 * | 5/2005 | Modglin | A61F 5/0193 | 128/882 |
| 7,766,850 B2 | 8/2010 | Simanovsky | | |
| 7,967,767 B2 | 6/2011 | Ogilvie | | |
| 8,066,653 B2 | 11/2011 | Seon | | |
| 8,409,122 B2 | 4/2013 | Cropper et al. | | |
| 8,657,769 B2 | 2/2014 | Ingimundarson et al. | | |
| 8,795,213 B2 | 8/2014 | Mills | | |
| 8,926,537 B2 | 1/2015 | Ingimundarson et al. | | |
| 8,945,034 B2 | 2/2015 | Ingimundarson et al. | | |
| 9,216,130 B2 * | 12/2015 | Killian | A61H 1/0292 | |
| 9,439,800 B2 | 9/2016 | Ingimundarson et al. | | |
| 2005/0059917 A1 * | 3/2005 | Garth | A61F 5/028 | 602/19 |
| 2008/0262402 A1 | 10/2008 | Ogilvie | | |
| 2011/0295170 A1 | 12/2011 | Laranjeira Gomes | | |

FOREIGN PATENT DOCUMENTS

| | | | |
|---|---|---|---|
| EP | 234372 | * | 9/1987 |
| EP | 0234372 A2 | * | 9/1987 |
| EP | 2457544 A1 | | 5/2012 |
| GB | 2467974 A | | 8/2010 |
| KR | 10-2010-0089953 | | 8/2010 |
| KR | 101070973 B1 | | 10/2011 |
| TW | M424137 U | | 3/2012 |
| WO | 2006068459 A1 | | 6/2006 |
| WO | 2010044796 A1 | | 4/2010 |

* cited by examiner

SCOLIOSIS BRACE

FIELD OF THE INVENTION

The field of the invention is orthotics.

BACKGROUND

The following description includes information that may be useful in understanding the present invention. It is not an admission that any of the information provided herein is prior art or relevant to the presently claimed invention, or that any publication specifically or implicitly referenced is prior art.

Scoliosis is a medical condition associated with an abnormally curved spine, often thought to be a progressive disease, at least until adulthood. Scoliosis can have severe adverse affects on a patient's life, both physically and physiologically. One possible method of treating or managing scoliosis is surgery. Unfortunately, scoliosis surgery can be very risky. Less invasive methods of treating or managing scoliosis has traditionally included physical therapy, chiropractic therapy, or bracing, among other things.

Some previous efforts have been made to provide improved comfort, support, or customizability to individual wearers. For example, U.S. Pat. No. 4,230,101 to Gold, U.S. Pat. No. 5,012,798 to Graf et al., International Patent Application Publication No. WO 2010/044796 to Ogilvie et al., International Patent Application Publication No. WO 2006.068459 to Van Loon et al., U.S. Pat. No. 5,405,313 to Albin, and UK Patent Application GB 2467974 to Mills teach various scoliosis management devices.

All publications or other extrinsic evidence herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Unfortunately, none of the above references teach a brace that provides both the desired level of comfort, support and modularity to a wearer. Thus, there is still a need for improved scoliosis braces.

SUMMARY OF THE INVENTION

The inventive subject matter provides apparatus, systems and methods in which a scoliosis brace is configured to provide adjustable support to a wearer. The brace preferably comprises a flexible belt configured to wrap around a mid-portion of a wearer, along with various components (e.g., struts, pads, adjustment mechanisms, etc.) configured to removably couple with the flexible belt and thereby provide customizable support to different portions of a wearer's body. A brace of the inventive subject matter can advantageously be configured to add a force or restrict a motion in the sagittal, transverse and coronal planes.

In one aspect of the inventive subject matter, a scoliosis brace comprises one or more vertical struts having an anchor pad (or base pad) coupled to a first strut, which is configured to removably attach to the interior side of the belt. It is contemplated that the anchor pad or the strut can removably attach to the belt in any commercially suitable manner, including for example, via a hook and loop fastener, snaps, buttons, magnets, and threading.

As used herein, a "vertical strut" is defined broadly to include a plurality of components (pads, struts, angle or height adjustment mechanisms, etc.) that are coupled with one another to create a single piece. As used herein, a "strut" is a single rod or bar forming a part of a framework. It can generally be preferred that a strut is made from either (1) a rigid material (e.g., a metal, a hard plastic, etc.) that requires more than an average person's force to bend, or (2) a material (e.g., aluminum, etc.) that is sized and dimensioned to be pliable when a strong force is applied, but sturdy when an ordinary force is applied.

A second strut can be coupled to the first strut and also be coupled with a thoracic pad configured to provide a pressure to a first side of the wearer below the underarm. It is contemplated that the first strut and the second strut can be movably coupled to one another such that one can rotate or pivot relative to the other.

It is also contemplated that the height of the thoracic pad relative to the central point of the anchor pad can be adjusted via any commercially suitable height adjustment mechanism, including for example, a rack and pinion mechanism, a biasing mechanism, a slidably coupled telescoped component, or any other commercially suitable component. Similar mechanisms can also be provided to adjust a horizontal position of the thoracic pad relative to the central point of the anchor pad.

A brace of the inventive subject matter can also comprise a first hip pad coupled to the first strut via a third strut, and configured to provide support to a hip area of a wearer. It is contemplated that the first strut and third strut can couple with one another to act as a height adjustment mechanism (e.g., to adjust a vertical position of the hip pad on the wearer relative to the central point of the anchor pad or an angle adjustment mechanism (e.g., to adjust a horizontal or vertical position of the hip pad on the wearer relative to the central point of the anchor pad).

In another aspect of the inventive subject matter, it is contemplated that the thoracic pad can be coupled to a curved arm configured to at least partially wrap around an upper chest portion of a wearer. The curved arm is preferably coupled to a de-rotation pad that is configured to put pressure on the upper chest wall on one side to cause a force intended to resist forward motion and rotation of that side of the chest when the brace is worn.

One or more straps can be provided and configured to couple with two or more components of the brace. For example, a first strap can be coupled to the belt (e.g., via hook and loop fastener, snaps, buttons, threading, zipper, or other commercially suitable fastener(s) or combinations thereof) and the thoracic pad (e.g., via a carabiner, a buckle, a button, a snap, or other commercially suitable fastener(s) or combinations thereof). A second strap can be configured to couple to at least two of the following, among other components: the de-rotation pad, the rounded arm, the first, second or third strut, the anchor pad, or the hip pad.

In some embodiments, a first vertical strut comprising the anchor pad, first strut, thoracic pad, de-rotation pad or hip pad can be coupled to the belt such that it provides support predominantly to a left or right side of the wearer. As used herein, the term "provides support predominantly to a left or right side" means that at least 80% of the components are located on a single side of the wearer. Thus, it is contemplated that a first vertical strut can be coupled to the belt such that it provides support predominantly to a left side of the wearer, even though 20% or less of the support is provided to the right side of the wearer. In some preferred embodiments, at least 90%, at least 95%, or even 100% of the support can be provided to a single side of the wearer via a first vertical strut. It is contemplated that additional components can be provided, if needed, via a second vertical strut to couple to the belt such that it provides support predominantly to the opposite side of the wearer.

The additional components can include a second anchor pad having a fourth strut and coupled to the belt, a second thoracic pad movably coupled to the second anchor pad via a fifth strut, a second de-rotation pad coupled to the second thoracic pad via a second rounded arm, a second hip pad, or any other suitable component(s).

Alternatively or additionally to being movably coupled to one another, each of the struts, straps, and pads can be removably coupled with, or attached to, another strut, pad, belt or other component of the inventive subject matter. Where a strut, pad or other component is moved from a first location to a second location, it is contemplated that the locations can be completely distinct or partially overlapping. For example, it is contemplated that a strut, pad or other component can be moved by as little as 5 cm, 2 cm, or even 1 cm or less, or can be moved by as much as 6 cm, 10 cm, or even 20 cm or even more.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It is contemplated that a brace of the inventive subject matter can utilize one or more of the components discussed in co-owned U.S. Pat. Nos. 7,001,348 and 8,142,377, and U.S. Patent Application Publication Nos. 2012/0232450 and 2012/0245502. For example, it is contemplated that a brace can utilize a pulley system as disclosed in U.S. Pat. No. 7,001,348.

Figure 1:
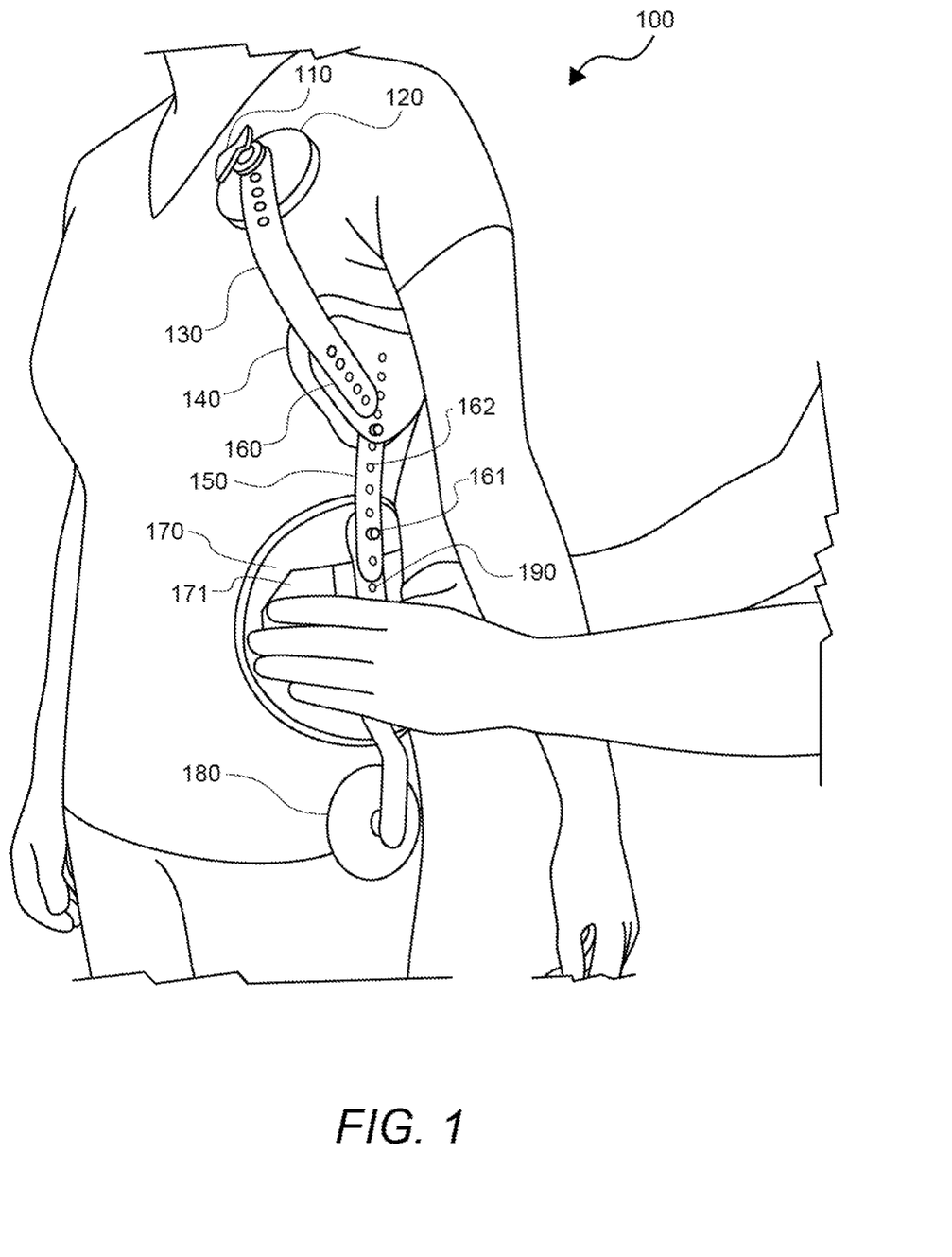
FIG. 1 shows one embodiment of a vertical strut of the inventive subject matter.

FIG. 1 shows a vertical strut 100 of the inventive subject matter. Vertical strut 100 is configured to provide support to a right or left side of a wearer, and preferably comprises an anchor pad 170 coupled with strut 190, a hip pad 180, a thoracic pad 140, rounded arm 130, and de-rotation pad 120 having a buckle receiver 110.

Anchor pad 170 comprises a hook or loop fastener 171 that is configured to removably attach to a belt (not shown). Contemplated pads can comprise any commercially suitable material(s), including for example, foam, silicon, nylon, cotton, mesh, or any other suitable material.

Strut 190 is coupled to angle/height adjustment mechanism 150 that allows a user to adjust a horizontal or vertical location of thoracic pad 140 relative to the anchor pad 170. One embodiment of such an angle/height adjustment mechanism is a second strut 162 and screw 161 mechanism. The horizontal location of thoracic pad 140 relative to anchor pad 170 can be adjusted via adjustment mechanism 150 by simply rotating the second strut 162 relative to the first strut 190. The vertical height of thoracic pad 140 relative to anchor pad 170 can be adjusted via adjustment mechanism 150 by unscrewing screw 161, adjusting the alignment of perforations on first strut 190 and second strut 162, and re-tightening screw 161.

In some other embodiments, it is contemplated that other angle or height adjustment mechanisms can be used, including for example, a series of snaps, a rack and pinion mechanism, a biasing mechanism, a slidably coupled telescoped component, or any other commercially suitable mechanisms.

Thoracic pad 140 can be coupled to curved arm 130 via a similar angle/height adjustment mechanism 160. Curved arm 130 is coupled with de-rotation pad 120, which advantageously provides support to an upper chest region of a wearer, and is configured to at least partially prevent a rotation of a patient's torso when worn, for example, by preventing a rotation of one or more components of the brace with respect to another component.

Figure 2:
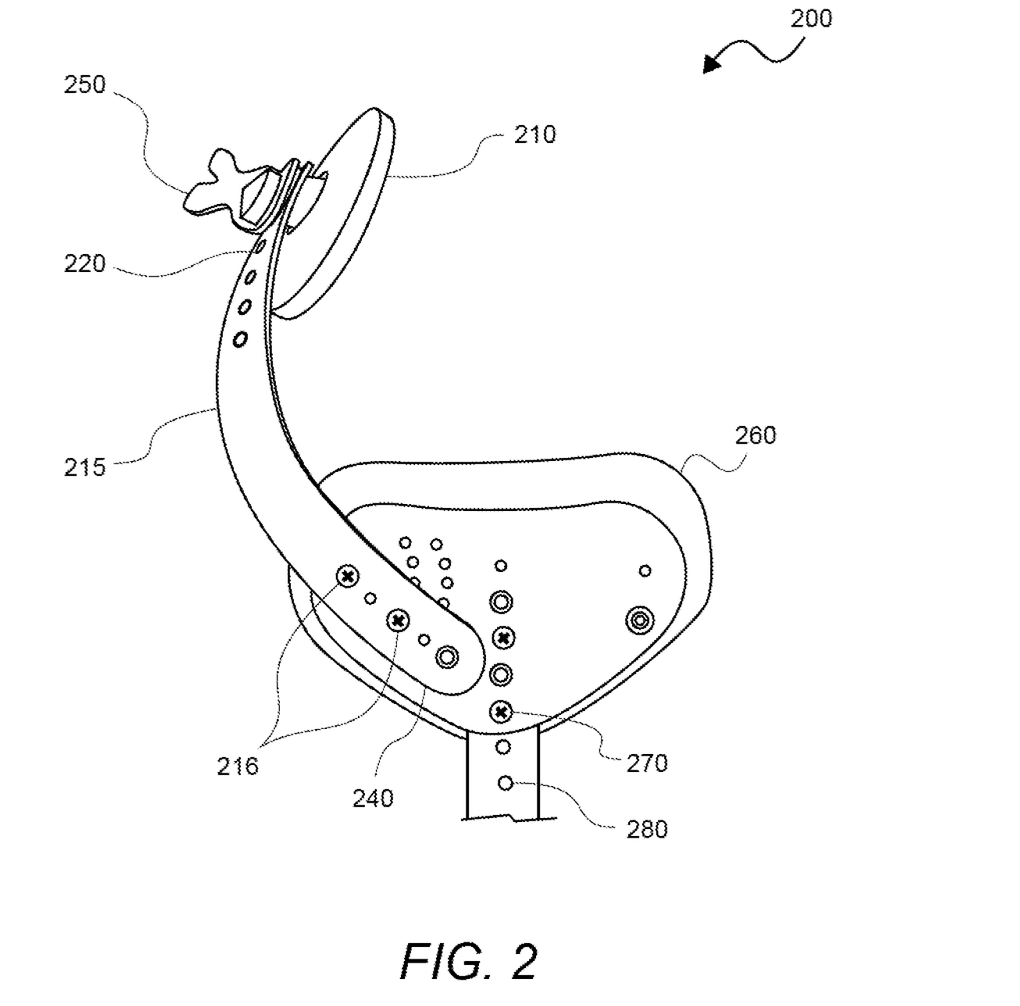
FIG. 2 shows one embodiment of a thoracic pad, rounded arm and de-rotation pad of the inventive subject matter.

FIG. 2 is a close up view of a thoracic pad, rounded arm and de-rotation pad of a vertical strut 200 of the inventive subject matter. Strut 280 is coupled to an anchor pad (not shown) and thoracic pad 260 via a fastener that also acts as a height adjustment mechanism 270. However, other types of fasteners could be used. Thoracic pad 260 is further coupled to curved arm 215, which can also acts as a part of height and angle adjustment mechanism 240 in conjunction with one or more fasteners 216. It is contemplated that a user can remove or loosen fasteners 216 and realign the perforations of curved arm 215 with a suitable perforation of thoracic pad 260 in order to adjust an angle or height of de-rotation pad 210 relative to thoracic pad 260.

De-rotation pad 210 can be coupled to curved arm 215 in any commercially suitable manner. However, it is currently preferred that de-rotation pad 210 and curved arm 215 are coupled together via a series of perforations and a snap configured to lock de-rotation pad 210 in a position aligned with one of the perforations.

De-rotation pad 210's fastener (height adjustment mechanism 220) is coupled to buckle receiver 250, which is configured to receive a buckle of a strap (not shown). A strap can be advantageously used to block a rotation of a component of the brace with respect to another component of the brace or providing a tension or tautness between the components to which it is attached. For example, a strap that is coupled to buckle receiver 250 and the belt can advantageously be used to block a change in a vertical position of a de-rotation pad relative to the belt, and further block a rotation of the vertical strut 200 comprising the de-rotation pad relative to the belt (alternatively or additionally to the blocking provided by a fastening mechanism between the belt and vertical strut).

Figure 3:
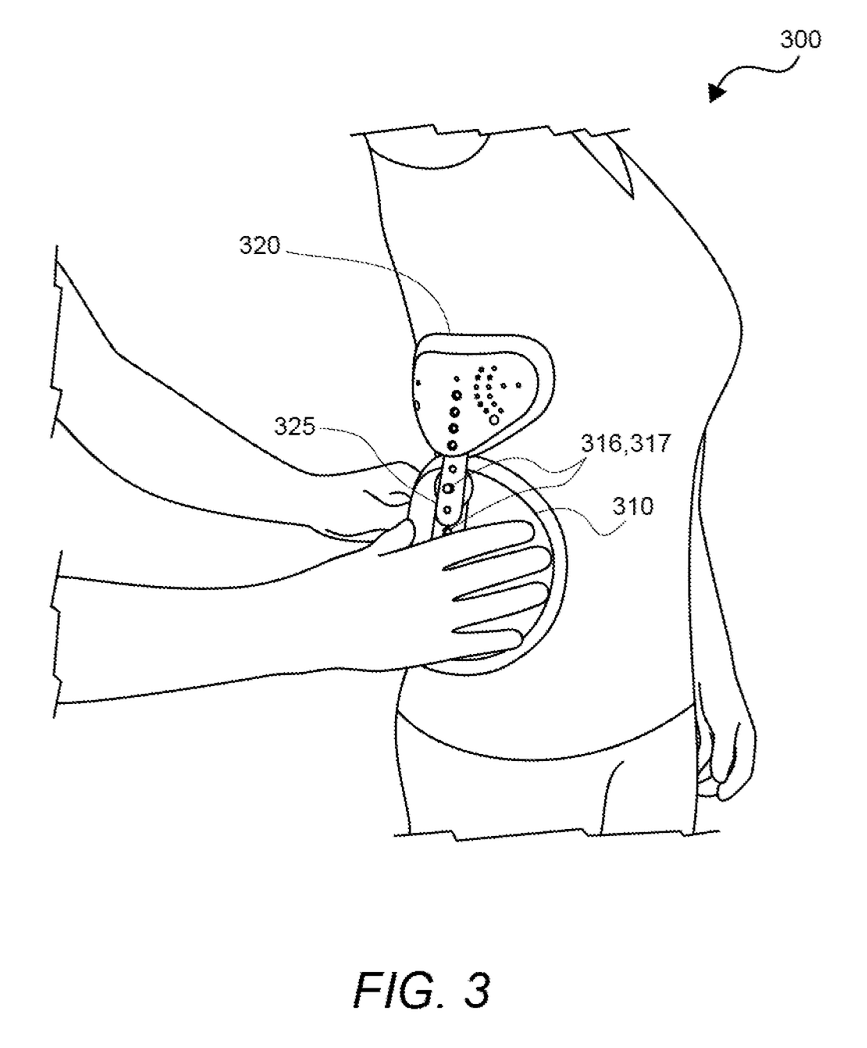
FIG. 3 shows one embodiment of another vertical strut of the inventive subject matter.

FIG. 3 shows a different vertical strut 300 of the inventive subject matter. Vertical strut 300 comprises an anchor pad 310, thoracic pad 320 and an angular and height adjustment mechanism 325 comprising a first and second strut, 316 and 317, respectively. It is contemplated that vertical strut 300 could also include additional components that are removable and adjustable with respect to the anchor pad 310 and thoracic pad 320. For example, vertical strut 300 could also comprise a third strut coupled with a hip pad, a rounded arm coupled with a de-rotation pad, or any other suitable component.

It is contemplated that vertical strut 100 or 200 could be worn on a right side of a wearer while vertical strut 300 is worn on a left side of a wearer, or vice versa.

Figure 4:
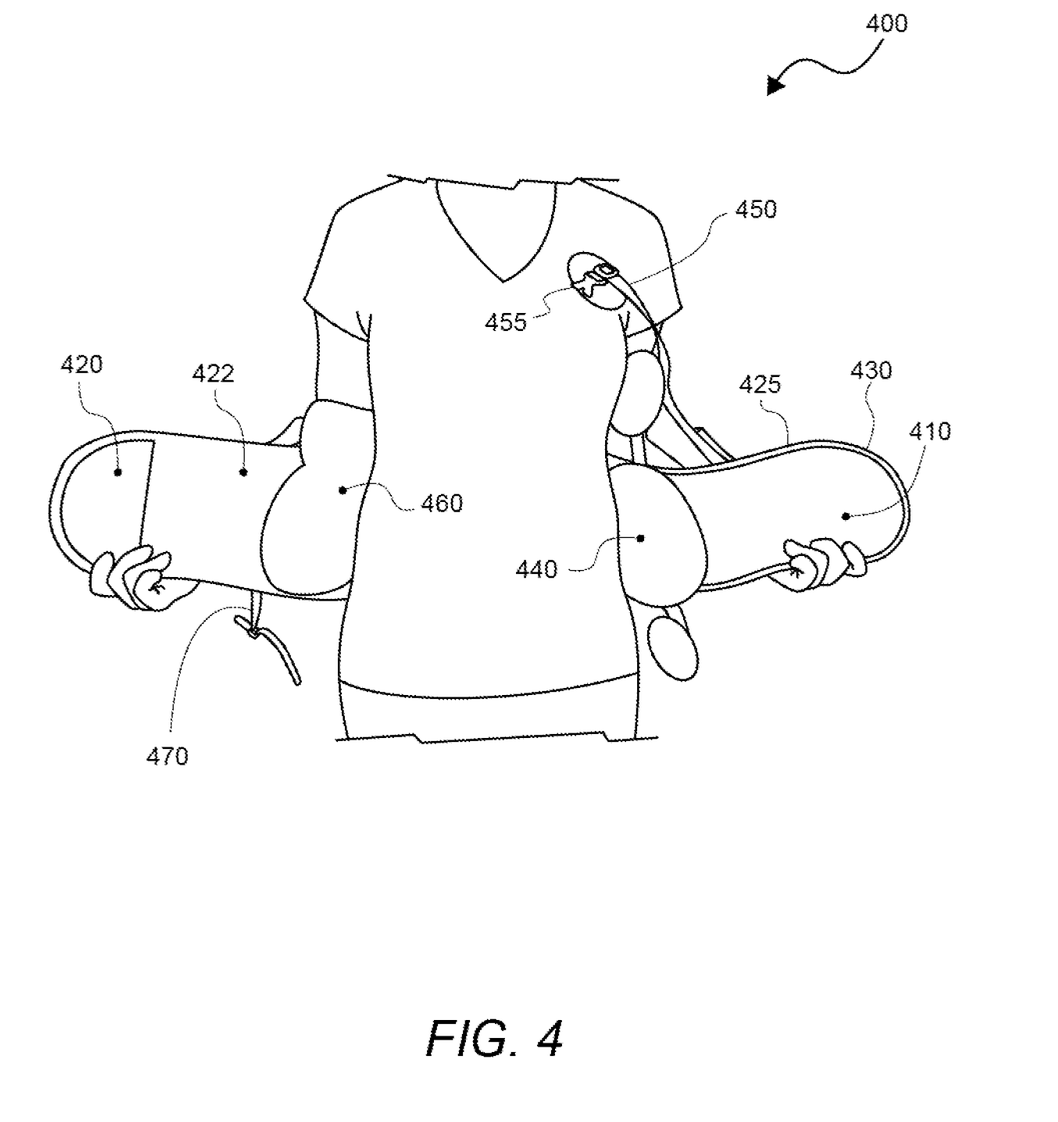
FIG. 4 shows one embodiment of a first and second vertical strut coupled to a flexible belt.

FIG. 4 shows a first vertical strut 440 and second vertical strut 460 each removably attached to a belt 410 of the inventive subject matter. Brace 400 comprises belt 410 having hook or loop fastener 420 on an inner side 422, and a complementary hook or loop fastener 430 on an outer side 425. Brace 400 also comprises a first vertical strut 440 removably attached to a left inner side of belt 400, and a second vertical strut 460 removably attached to a right inner side of belt 400.

Belt 410 is preferably configured to wrap around a mid-portion of a wearer and securely fasten to itself via hook or loop fasteners 420 and 430, although any commercially suitable fasteners could be used. First strap 470 is coupled with a first attachment point (on outer side 425) on the outer side of belt 400, and is configured to couple with a thoracic pad of second vertical strut 460, and de-rotation pad 450 of first vertical strut 440 via buckle receiver 455. First strap 470 and de-rotation pad 450 can be advantageously used together to cause an increase in pressure on a portion of the patient to support them in a desired position.

One having ordinary skill in the art should appreciate that references to a "fastener" are used broadly to refer to any commercially suitable fastener(s), including for example, a hook and loop fastener, a button, a snap, a belt type buckle, a side squeeze buckle, a magnet, a zipper, perforations and screws or snaps, or any other commercially suitable fastener(s). One having ordinary skill in the art should also appreciate that some fasteners can also serve as, or be coupled with, an adjustment mechanism such as a length, height, angle or other adjustment mechanism.

Figure 5:
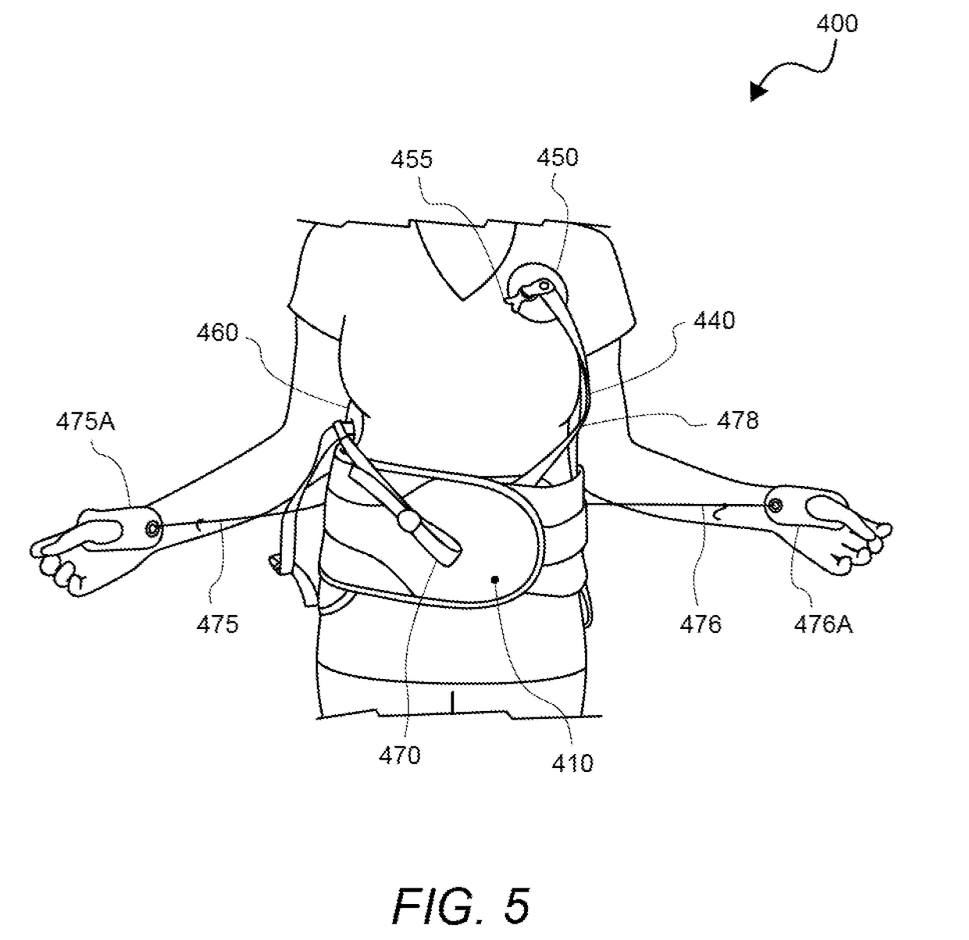
FIG. 5 shows one embodiment of a brace of the inventive subject matter as worn by a wearer.

FIG. 5 shows the brace 400 of FIG. 4 as partially fastened to a wearer. As shown, belt 410 has been fastened to itself around a mid-portion of the wearer via hook and loop fasteners, and the brace 400 is being tightened via first cord system 475 and second cord system 476. It is contemplated that the pull tabs of cord systems 475 and 476 (e.g., 475A and 476A) can comprise a hook or loop fastener that can removably attach to a hook or loop fastener of the outer side of belt 400. As discussed above, it is contemplated that a brace of the inventive subject matter can utilize one or more of the components discussed in co-owned U.S. Pat. Nos. 7,001,348 and 8,142,377, and U.S. Patent Application Publication Nos. 2012/0232450 and 2012/0245502. For example, it is contemplated that a brace can utilize a pulley system as disclosed in U.S. Pat. No. 7,001,348.

Brace 400 comprises a second strap 478, which is fastened to an outer side of belt 400 via any suitable fastener (e.g., hook or loop, snaps, buttons, etc.) and further coupled to a thoracic pad of first vertical strut 440.

Figure 6:
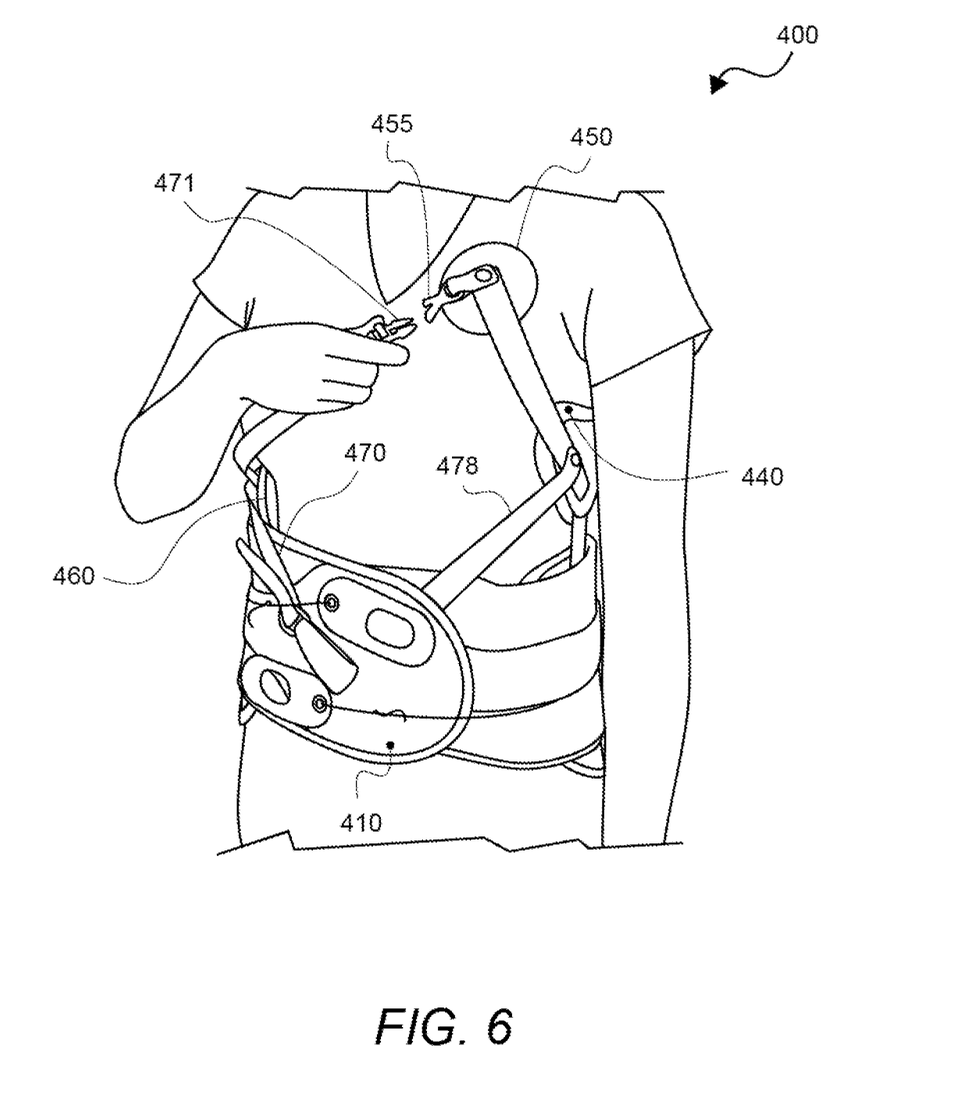
FIG. 6 shows one embodiment of a strap of the inventive subject matter having a buckle.

FIG. 6 shows a front-left side view of the brace 400 of FIGS. 4 and 5. First strap 470 is attached to belt 410 and second vertical strut 460, and is shown in being fastened to buckle receiver 455 of de-rotation pad 450 via buckle 471 of first strap 470. Second strap 478 is removably fastened to belt 410 and removably fastened to the thoracic pad of first vertical strut 440 via a screw that also acts as part of an angle and height adjustment mechanism between the curved arm and thoracic pad of first vertical strut 440.

Figure 7:
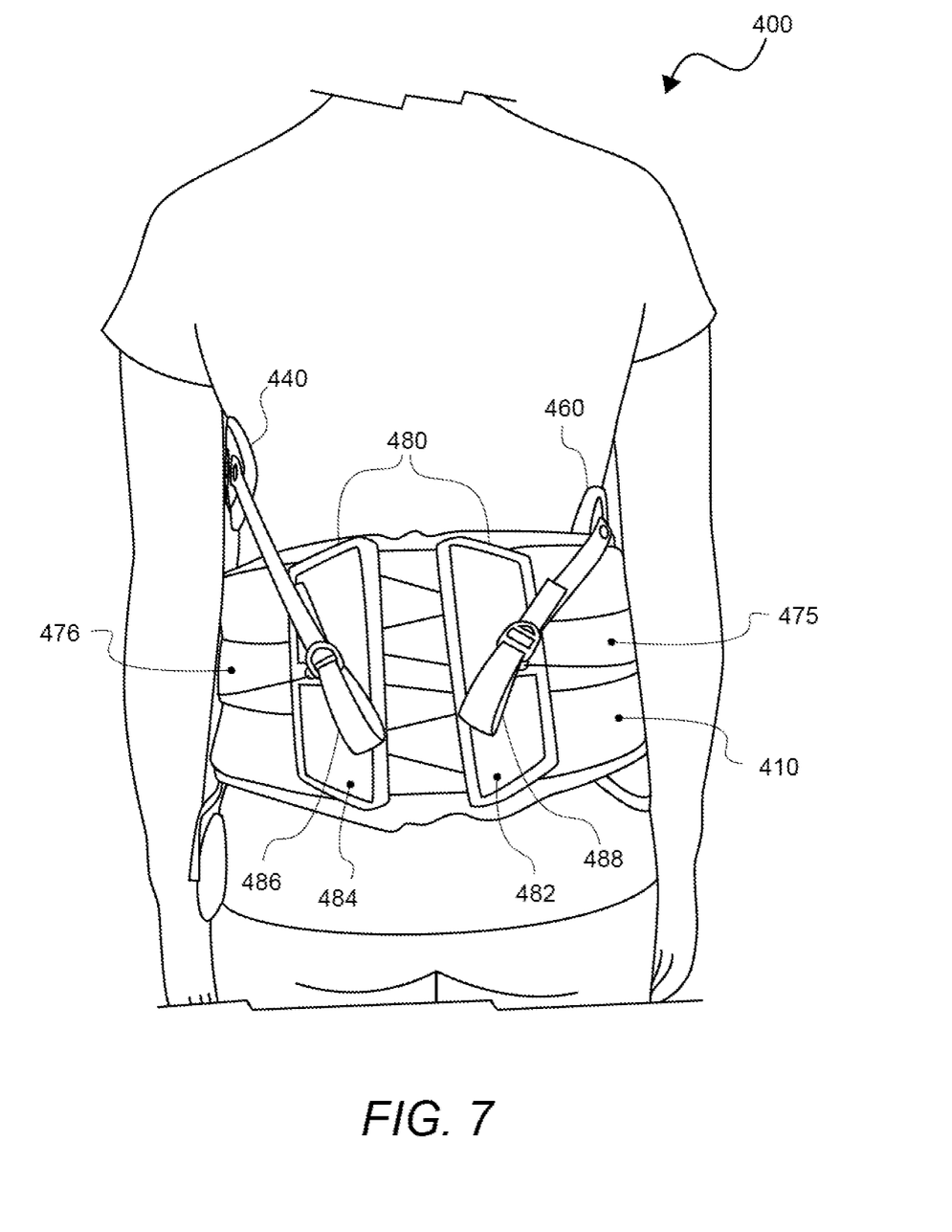
FIG. 7 shows one embodiment of a rear portion of a brace of the inventive subject matter.

FIG. 7 shows a back view of the brace 400 shown in FIG. 4 as worn by a wearer. Brace 400 comprises a tightening mechanism 480 shown in having two cord systems 475 and 476. It is contemplated that first cord system 475 can be configured to tighten a top portion of belt 410 (e.g., shorten a distance between the top portion of right cord guide cover 482 and left cord guide cover 484) when pulled in a first direction, while second cord system 476 can be configured to tighten a bottom portion of belt 410 (e.g., shorten a distance between the bottom portion of right cord guide cover 482 and left cord guide cover 484) when pulled in a second direction different from the first direction. Alternatively, each cord could be used to tighten a top and a bottom portion of belt 410.

Brace 400 further comprises a third strap 486 and fourth strap 488. Third strap 486 is configured to attach to left cord guide cover 484 and first vertical strut 440 via any suitable fastening means, and fourth strap 488 is configured to attach to right cord guide cover 482 and second vertical strut 460 via any suitable fastening means.

The combination of first, second, third and fourth straps (470, 478, 486, and 488) can be used together to provide increased support to a wearer while ensuring that a proper amount of force is being applied to the areas intended.

Figure 8:
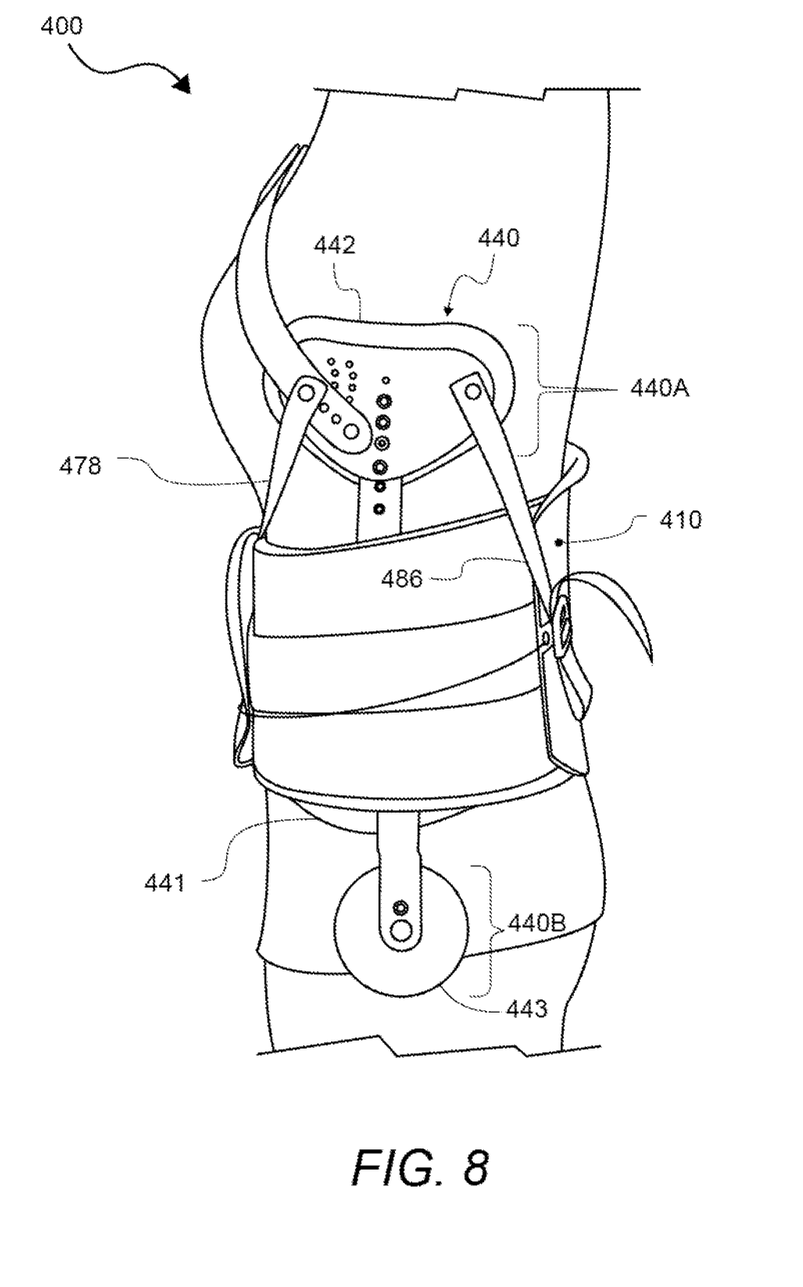
FIG. 8 shows one embodiment of a side portion of a brace of the inventive subject matter.

FIG. 8 is a left side view of the brace 400 of FIGS. 4-7 showing first vertical strut 440 attached to an inner side of belt 410. As shown, anchor pad 441 is substantially aligned with the height of belt 410. Vertical strut 440 is configured to provide pressure to at least two portions of the wearer's body. The first area 440A is the left side of the wearer between the underarm and mid-portion, which is supported by thoracic pad 442. The second area 440B is the left hip of the wearer, which is supported by hip pad 443.

Second strap 478 and third strap 486 are each fastened to belt 410 and thoracic pad 442, and are configured to provide an adjustable amount of tension or tautness between the two components to which they are attached, or prevent a rotation of one component (e.g., the thoracic pad 442) relative to another component (e.g., the midline of the belt where the belt could be folded in half along its length) to thereby prevent a rotation of a patient's body, or adjust the patient's body back into a less rotated state.

Figure 9:
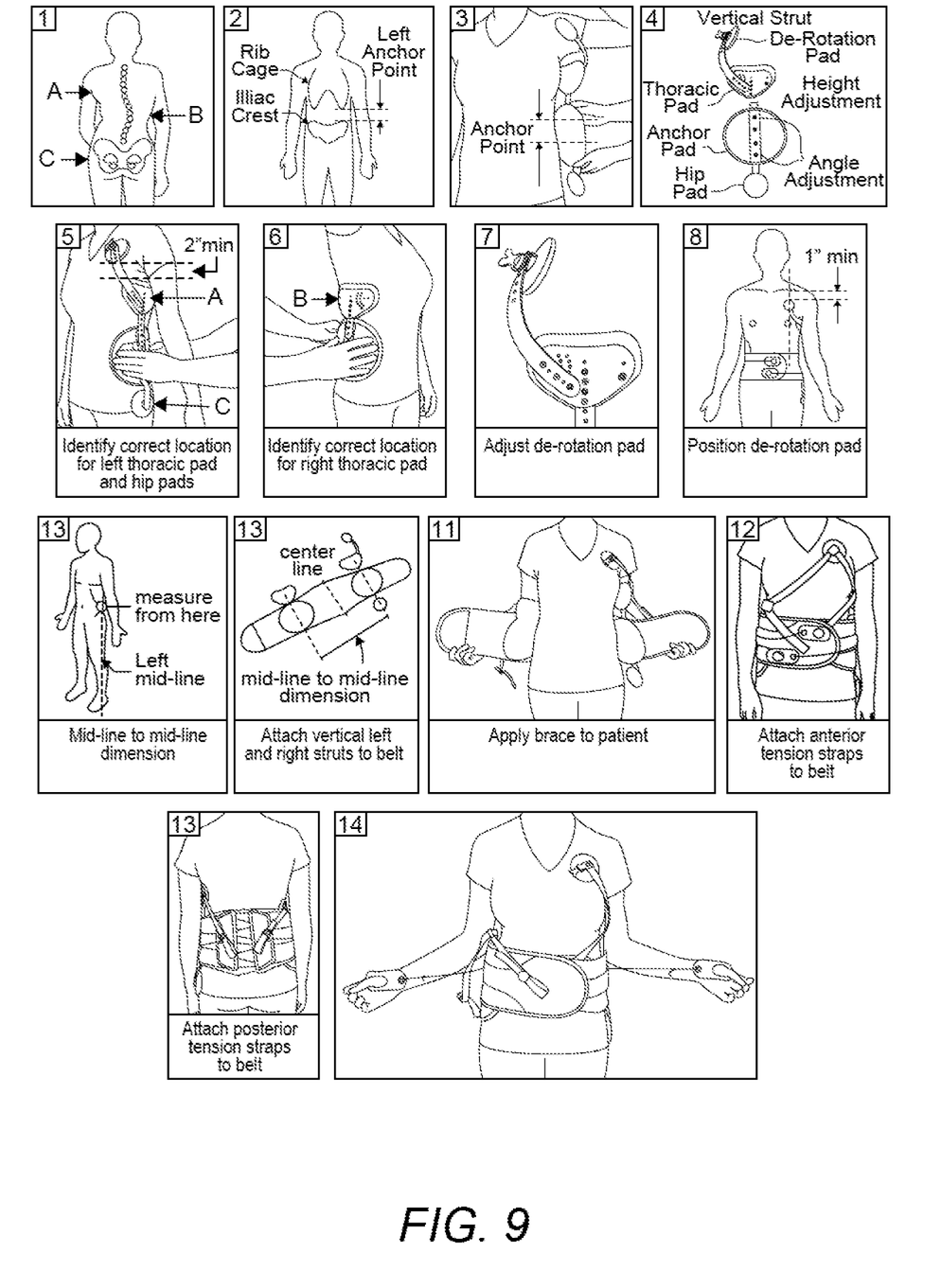
FIG. 9 shows a step by step flowchart of one method of fitting a wearer with a brace of the inventive subject matter.

FIG. 9 provides a step by step flowchart of one method of fitting a wearer with a brace.

As shown in step 1, a healthcare professional or other person can obtain an x-ray of a wearer's spine to identify a curve apex and locations where force should be applied. For example, step 1 shows that force should be applied at points A, B and C.

Step 2 shows how to locate an anchor point to which the anchor pad can be aligned. The left anchor point, for example, is located between the rib cage and iliac crest of the wearer. Depending on the curvature of the wearer's spine or other factors, it is contemplated that the anchor point(s) can alternatively be in a location other than between the rib cage and iliac crest.

Step 3 shows a vertical strut being fit on a wearer based on the anchor pad's alignment with the left anchor point. Once the location of the anchor pad is determined, the remaining components of the vertical strut can be adjusted (e.g., bending of the strut, adjustment of the relative heights of each component, adjustment of an angle between components, etc.) to provided a force to the intended areas of a user (e.g., areas A and C of step 1) as shown in Steps 4 and 5.

Step 4 shows a possible arrangement of components of a vertical strut. Step 5 shows that the thoracic pad of the first vertical strut can align with force point A. In this embodiment, it is generally preferred that at least two inches separate the underarm of the wearer and the top portion of the thoracic pad. In this embodiment, a Phillips screw driver can be used to align the thoracic and hip pads with previously identified locations where force will be applied.

Step 6 shows a second vertical strut being fit on the wearer based on a second anchor pad's alignment with the right anchor point. The thoracic pad of the second vertical strut is applied to force point B identified Step 1, which represents a curve apex of the wearer's spine.

Step 7 shows how a de-rotation pad of the first vertical strut can be adjusted to fit the wearer. In this embodiment, the top edge of de-rotation pad is adjusted to be 1 inch below the clavicle of the wearer and directly above the nipple, as shown in Step 8. The de-rotation pad can be coupled to a curved arm or strut, which in this embodiment comprises bendable aluminum. This curved arm or strut can serve as an additional angle adjustment mechanism.

Once the first and second vertical struts have been adjusted to fit the wearer's body, a measurement can be taken between the wearer's left mid-line and the wearer's right mid-line as shown in Step 9.

Each of the first and second vertical struts can comprise a hook or loop fastener that is configured to removably fasten with a hook or loop fastener of either an inner or outer side of the belt (inner side shown here) as shown in Step 10. The center line of the belt should be identified, and either strut should be attached on opposing sides of the center line such that a distance between the midlines of each anchor pad equals the distance between the left mid-line and the right mid-line previously measured in accordance with Step 9.

Step 11 shows a wearer putting on the brace after the first and second vertical struts have been fit and attached to the belt in accordance with Steps 1-10. The wearer aligns the anchor pads of each strut with the left or right anchor points and wraps the belt such that the ends of the belt overlap and fasten to one another. As shown in Step 12, the first end of the first and second tension straps are then attached to the belt. A mid portion of the first tension strap is then attached to the second vertical struts thoracic pad, and a second end of the first tension strap is coupled with de-rotation pad via a buckle. The second end of the second tension strap is attached to the thoracic pad of the first vertical strut via a screw mechanism.

Step 13 shows third and fourth tension straps each attached to the belt and a different component of the brace. Step 14 shows the wearer tightening the brace through first and second cord systems that are pulled in opposite directions and fastened to the belt via pull tabs.

It is contemplated that a brace of the inventive subject matter can alternatively or additionally comprise other components, including for example, a lumbar pad, an underarm support, or a chest support pad.

Figure 10:
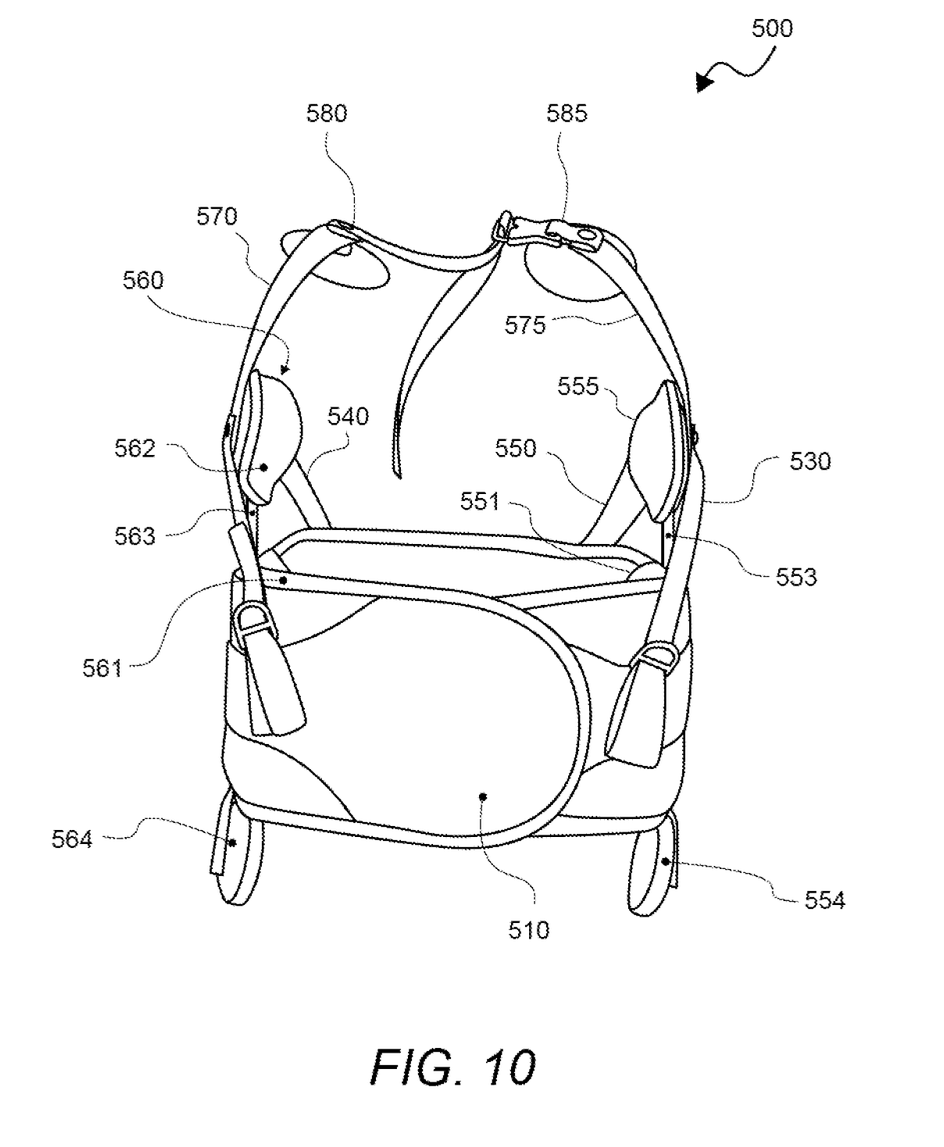
FIG. 10 shows another embodiment of a brace of the inventive subject matter having substantially similar left and right vertical struts with removable and adjustable components.

FIG. 10 shows another brace 500 of the inventive subject matter having substantially similar left and right vertical struts with removable and adjustable components. Brace 500 comprises a belt 510, a first tension strap 520, second tension strap 530, third tension strap 540, fourth tension strap 550, a first vertical strut 555 comprising a first anchor pad 551 having a first strut (not shown), a first thoracic pad 552 having a second strut 553, a first hip pad 554 having a third strut (not shown), and a second vertical strut 560 comprising a second anchor pad 561 having a fourth strut (not shown), a second thoracic pad 562 having a fifth strut 563, and a second hip pad 564 having a sixth strut (not shown).

The second strut (e.g., 553) and third strut are removably and adjustably coupled with first strut such that an angle or vertical position of the first thoracic pad and first hip pad can be adjusted relative to the first anchor pad, or even removed. Similarly, the fifth strut (e.g., 563) and sixth strut are removably and adjustably coupled with third strut such that an angle or vertical position of the second thoracic pad and second hip pad can be adjusted.

Each of the first and second thoracic pads are coupled with a rounded arm, 570 and 575, which are in turn coupled with de-rotation pads, 580 and 585. The first and second straps are removably attached to the front portion of belt 510 and a thoracic pad, while the third and fourth straps are removably attached to the back portion of belt 510 and a thoracic pad. When the brace is worn, the tension straps can both block a rotation of a component of the brace relative to other components and provide increased tension or tautness between components of the brace.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A scoliosis brace, comprising:
   an upper torso pad configured to be positioned on a lateral side of a wearer;
   a lower torso pad having a wearer-facing side and configured to be positioned on the lateral side;
   a hip pad having a wearer-facing side that is smaller than the wearer-facing side of the lower torso pad, wherein the hip pad is configured to be positioned on the lateral side;
   an upper strut coupling the upper torso pad with the lower torso pad and configured to be positioned on the lateral side;
   a lower strut coupling the lower torso pad with the hip pad and configured to be positioned on the lateral side; and
   a flexible belt configured to wrap around left and right sides of a mid-portion of the wearer, and overlay both the lower torso pad and the lower strut;
   wherein the upper torso pad, lower torso pad, and hip pad are configured to be vertically aligned along the lateral side of the wearer.

2. The brace of claim 1, further comprising an anterior connector configured to couple the upper torso pad with an anterior portion of the belt with respect to the upper strut when the brace is worn.

3. The brace of claim 2, further comprising a posterior connector configured to couple the upper torso pad with a posterior portion of the belt with respect to the upper strut when the brace is worn.

4. The brace of claim 1, further comprising an anteriorly positioned upper torso pad, coupled to the upper torso pad configured to be positioned on the lateral side using a curved strut.

5. The brace of claim 1, wherein the flexible belt is configured to be positioned above the hip pad when the brace is worn.

6. The brace of claim 1, wherein the upper strut has multiple mechanical couplings configured to provide height adjustment between the upper torso pad and the lower torso pad.

7. The brace of claim 1, wherein the lower strut has multiple mechanical couplings configured to provide height adjustment between the hip pad and the lower torso pad.

8. The brace of claim 1, further comprising a posterior connector configured to couple the upper torso pad with a posterior portion of the belt with respect to the upper strut when the brace is worn.

* * * * *